(12) United States Patent
Sevincli

(10) Patent No.: US 11,565,070 B2
(45) Date of Patent: Jan. 31, 2023

(54) COAXIAL BREATHING CIRCUIT SYSTEMS HAVING A LUNG PRESSURE MEASUREMENT PORT AND CLOSED SYSTEM WATER TRAP WHICH CAN BE DRAINED WITH AN ENJECTOR

(71) Applicants: MEDITERA TIBBI MALZEME SANAYI VE TIOARET A.S., Izmir (TR); Atilla Sevincli, Izmir (TR)

(72) Inventor: Atilla Sevincli, Izmir (TR)

(73) Assignees: MEDITERA TIBBI MALZEME SANAYI VE TIOARET A.S., Izmir (TR); ATILLA SEMNCI, Izmir (TR)

( * ) Notice: Subject to any disclaimer, the term of this patent is extended or adjusted under 35 U.S.C. 154(b) by 357 days.

(21) Appl. No.: 16/802,642

(22) Filed: Feb. 27, 2020

(65) Prior Publication Data

US 2020/0197648 A1   Jun. 25, 2020

Related U.S. Application Data

(62) Division of application No. 15/745,129, filed on Jan. 15, 2018, now Pat. No. 11,395,896.

(51) Int. Cl.
*A61M 16/08*    (2006.01)
*A61B 5/087*    (2006.01)
*A61B 5/08*     (2006.01)

(52) U.S. Cl.
CPC .......... *A61M 16/0808* (2013.01); *A61B 5/082* (2013.01); *A61B 5/087* (2013.01); *A61M 16/0833* (2014.02); *A61M 16/0875* (2013.01)

(58) Field of Classification Search
CPC .............. A61M 16/00; A61M 16/0003; A61M 2016/0015–0042; A61M 16/08–0883; A61M 16/0808–0841; A61M 16/0875–0891; A61M 16/0078; A61M 16/085; A61M 16/107; A61M 2205/7518; A61B 5/082; A61B 5/087; Y10S 128/911; Y10S 128/912
USPC ........................................ 128/205.12, 205.27
See application file for complete search history.

(56) References Cited

U.S. PATENT DOCUMENTS

| | | | |
|---|---|---|---|
| 6,209,539 B1 * | 4/2001 | Loescher | A61M 16/0858 128/204.17 |
| 2005/0010189 A1 * | 1/2005 | Toomey | A61B 5/150389 604/403 |
| 2010/0122702 A1 * | 5/2010 | Reinboth | A61M 16/0808 128/205.27 |
| 2010/0252035 A1 * | 10/2010 | Chang | A61M 16/0875 128/200.24 |

(Continued)

FOREIGN PATENT DOCUMENTS

EP    3090774 A1 * 11/2016 ............ A61M 16/01

*Primary Examiner* — Elliot S Ruddie
(74) *Attorney, Agent, or Firm* — Bayramoglu Law Offices LLC

(57) ABSTRACT

The invention relates to providing novel functions to the coaxial breathing circuits which at present do not comprise water traps, by adding a closed system water trap designed to have an inkwell shape and a lung pressure measurement port to said circuits wherein the fluid collected in the bottle section can be discharged without having to open the bottle by means of a drainage luer port located at the base of the bottle and a needleless apparatus that has been inserted into the port, and an injector.

7 Claims, 9 Drawing Sheets

(56) References Cited

U.S. PATENT DOCUMENTS

2012/0017907 A1\* 1/2012 Hsiao ................ A61M 16/0808
  128/205.12
2014/0150794 A1\* 6/2014 Kendrick .......... A61M 16/0808
  128/205.12

\* cited by examiner

COAXIAL BREATHING CIRCUIT SYSTEMS HAVING A LUNG PRESSURE MEASUREMENT PORT AND CLOSED SYSTEM WATER TRAP WHICH CAN BE DRAINED WITH AN ENJECTOR

CROSS REFERENCE TO RELATED APPLICATION

This application is a divisional application of application Ser. No. 15/745,129 filed on Jan. 15, 2018, which is the national phase entry of International Application No. PCT/TR2015/050066, filed on Aug. 13, 2015, the entire contents of which are incorporated herein by reference.

TECHNICAL FIELD

The invention relates to a respiratory system, especially relates to a double lumen and coaxial breathing circuit systems that have been redesigned with a lung pressure measurement port at the patient side and with closed system water trap that have been designed having inkwell shapes, which can be drained with an injector and a needleless apparatus that has been placed into the port.

BACKGROUND OF THE INVENTION

Nowadays mechanical ventilation is applied using a ventilation device in order to provide sufficient oxygen to the blood in case of difficulty in breathing during operations or in intensive care units. An anaesthesia device is used however during operations to perform anaesthesia procedures. The systems which provide gas flow between the patient and the devices are called anaesthesia and ventilation circuits. The circuits are formed of generally three types such as double tube (conventional), coaxial double tube (coaxial) and single tube divided into two with a membrane (double lumen).

As a result of excretions received from the respiratory system of the patient under anaesthesia or using mechanical ventilation and condensation of the water vapour, fluids that may have infection risks are collected at the expiratory side of the tubes that constitute the breathing circuits. Besides this, fluid accumulation is formed in the inspiratory line of the breathing circuit as the certain rate of breath received from the patient is present inside the anaesthetic gas that is applied to the patient during low flow rate anaesthesia.

In intensive care units breathing circuits are applied to the patients for long periods of time. As the air received from ventilation devices is dry and cold, the air supplied to the patient needs to be humidified and heated in order for the respiratory tract of the patient not to be damaged. When the heated and humidified air is exposed to the cold atmosphere of the intensive care unit, water condensation occurs.

Accumulated fluid cause resistance against the air flow from the breathing circuit tubes. For this reason a water trap is required in order to prevent the accumulation of fluid in anaesthesia circuits during long duration operations for circuits used for anaesthesia, and to retain fluids received from the patient and the humidity that has condensated in breathing circuits used in intensive care units. In conventional circuits water trap are provided.

Water trap mechanism is not provided in the present double lumen breathing circuits. As the standard water traps cannot be used in double lumen breathing circuits due to the design of the leg part that is used to attach water traps to the breathing circuit tubes, the water that accumulates at the tube of double lumen breathing tube cannot be drained from the mid section of the tube where it accumulates the most. The present double lumen breathing circuits are therefore not being used in intensive care units, and during the anaesthesia applied in long duration operations, due to fluid accumulation problem in both expiratory and the inspiratory line.

Conventional water traps are installed at the point of the tube (expiratory line) where it is coupled to the anaesthesia device, wherein the breath of the patient is transferred from said tube; in order to prevent the flow of water to the anaesthesia device from the double lumen breathing circuits.

While the patient is taken to the intensive care unit following an operation the double lumen breathing system that has been used during operation for anaesthesia is replaced as it does not comprise a water trap with a breathing circuit comprising a water trap. This causes extra costs for the hospital. As the water traps that are used in the intensive care unit fill up with water, the bottle located below the system is opened by a nurse and the fluid is discharged. During this procedure, as the breathing system remains open to the external environment when the bottle of the water trap is opened, the risk of the nurse to be infected from the patient and the risk of the patient to be infected from both the external environment and the nurse is present.

The lung pressure measurement port, is located at the line where the breath of the patient passes through in conventional breathing circuits and the port enables to determine if the required pressure difference for the patient to be able to breath is formed or not and if the patient perform carbon dioxide re-breathing or not. Lung pressure measurement cannot be carried out in the present double lumen and coaxial breathing circuits, as the present structure of the I connector of these breathing circuits remaining at the side that is connected to the patient is not suitable.

The patent document numbered US2010122702 (A1) of the known state of the art is related to an inner gas channel (3) which separates condensate and a co-axial tube system having an outer gas channel (4). The first fluid channel (10), has been arranged between an inner gas channel and a first collection volume (8) and the second fluid channel (11) has been arranged between the outer gas channel (4) and the second collection volume (9). The collection units (8,9) are together with a fluid collection bottle (6) having partitions (7) between them. It has been ensured that the water trap is not opened manually in the related patent and that the water is discharged periodically by means of vacuum created via a connection from the top of the retainer. A vacuum device is required in order to discharge the accumulated water.

According to the patent document of the known state of the art numbered U.S. Pat. No. 4,867,153 (A) the invention is related to discharging fluid accumulated into the tubes and then into the bottle of the breathing system due to respiration, without any contact of the fluid with a person. In said sealed drainage system a valve is provided underneath the bottle. Said valve is operated manually. The water trap is able to retain the water in both the inspiratory and the expiratory lines and is able to collect the water in different chambers. The drainage of the accumulated water is performed by opening the chambers one by one. At this point, the inspiratory and expiratory gasses do not mix with each other by means of the developed valve system and air leakage from the breathing circuit is not experienced.

When the documents of the known state of the art and the present applications are taken into consideration, it can be said that the invention has been designed to be used in both conventional and the double lumen breathing systems that presently do not comprise water traps. The invention is able to retain the water from both the inspiratory (where air is submitted to the patient) and the expiratory (air is received from the patient) lines of both of the (coaxial and double lumen) breathing circuits. The collected water can be easily discharged by means of a connector that can be attached via a luer lock to the water trap and a connector attached to the end of an injector. Moreover the water traps (water traps of the inspiratory and expiratory lines) that are used in coaxial breathing circuits can both be used with a bottle not having a luer connection if preferred and a conventional stopper instead of an inkwell structure. When the water trap of the coaxial breathing circuit expiratory line is desired to be used with a conventional breathing circuit closed system, said circuits can also be used. Besides this, lung pressure measurement ports have been attached to the double lumen and coaxial breathing circuits which at present do not comprise said ports.

US2014/150794A1 discloses fluid trap for a dual lumen breathing circuit with leg sections with connections to the breathing circuit.

US2010/122702A1 discloses a condensate separator for a coaxial breathing circuit including an expiratory line tube coupling and an inspiratory enabling collection of water that has accumulated inside the inspiration line.

U.S. Pat. No. 4,867,153A discloses a needleless apparatus which enables the drainage of water collected in the bottle section.

DE3823242A1 discloses a grooved luer port used for draining fluid.

U.S. Pat. No. 5,404,873 discloses a monitoring port in a coaxial breathing circuit.

SUMMARY OF THE INVENTION

The invention is related to a closed system, water trap, lung pressure measurement port, double lumen and coaxial breathing circuit system from which fluid can be discharged by an injector that has been designed to be able to discharge the water from both the inspiratory (air is submitted to the patient) and the expiratory (air is received from the patient) lines that retain water both from double lumen breathing circuits, that do not comprise water traps at present, and coaxial breathing circuit from the water trap into which water has been collected by a luer and a connector that can be attached to an injector. Moreover the water traps (water traps of inspiratory and expiratory lines) that are used in coaxial breathing circuits can be used with a bottle not having a luer connection if desired or with a conventional stopper instead of an inkwell form and additionally, lung pressure measurement ports have been attached to double lumen and coaxial breathing circuits. Besides this in the case that water traps compliant with coaxial breathing circuits are desired to be used with closed system water traps, conventional breathing circuits can also be used.

A water trap can be used in the middle of the tube which is the point where most of the water accumulates in the breathing circuits of closed system water traps and double lumen breathing circuits developed according to the invention.

By means of the new closed system water traps, the water that accumulates both in the section where air is received from the patient and where air is submitted to the patient in the double lumen and coaxial breathing systems are retained and the resistance against the air flow is eliminated and also the risk of leakage of water into the anaesthesia and ventilation devices are also overcome.

By means of the novel design and structures of the closed system water traps that can be used with coaxial, conventional and double lumen breathing circuits, the fluid that is accumulated in the bottle section of the water traps can be discharged with an injector without using a needle and without disrupting the closure of the closed system. Thereby the risk of the patients to be infected with diseases arising from ventilation and hospital environment is reduced. The possibility of the nurses to be contact with patient fluids which carry high infection risks is also eliminated.

The double lumen and coaxial breathing circuits can carry out lung pressure measurements by means of the connector having lung pressure measurement port attached thereon.

BRIEF DESCRIPTION OF THE DRAWINGS

The figures that have been prepared in order to better illustrate the closed system water traps which can be discharged with an injector developed according to the present invention and the double lumen and coaxial breathing circuit systems having a lung pressure measurement port have been described below.

DEFINITIONS OF THE PARTS FORMING THE INVENTION

The parts in the figures which have been drawn in order to further explain the double lumen and coaxial breathing circuits having a lung pressure measurement port and closed system water trap that can be discharged with an injector developed by means of this invention have each been numbered and the references of each number have been listed below.

Figure 5:
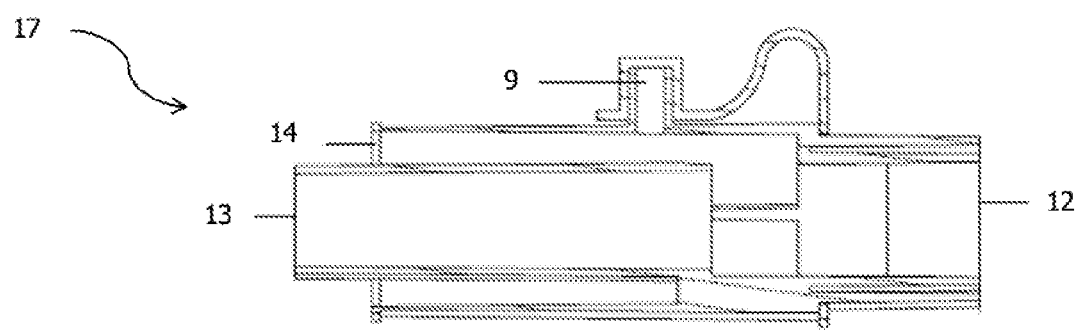
FIG. 5—Is the vertical view of the I connector comprising a lung pressure measurement port for a coaxial breathing circuit.
Figure 6:
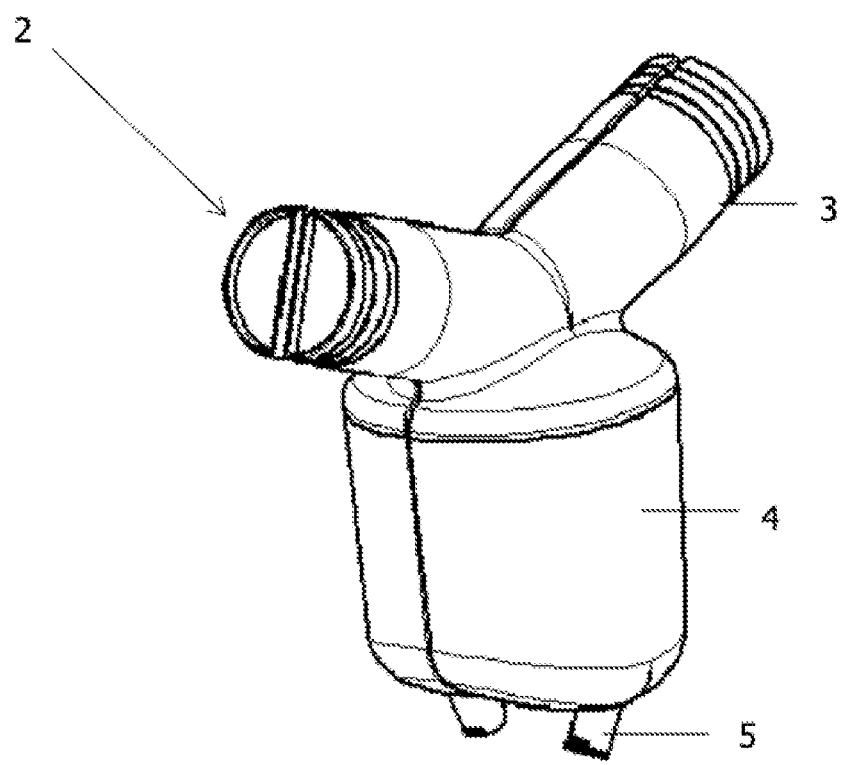
FIG. 6—Is the perspective view of the closed system water trap for a double lumen breathing circuit.
Figure 7:
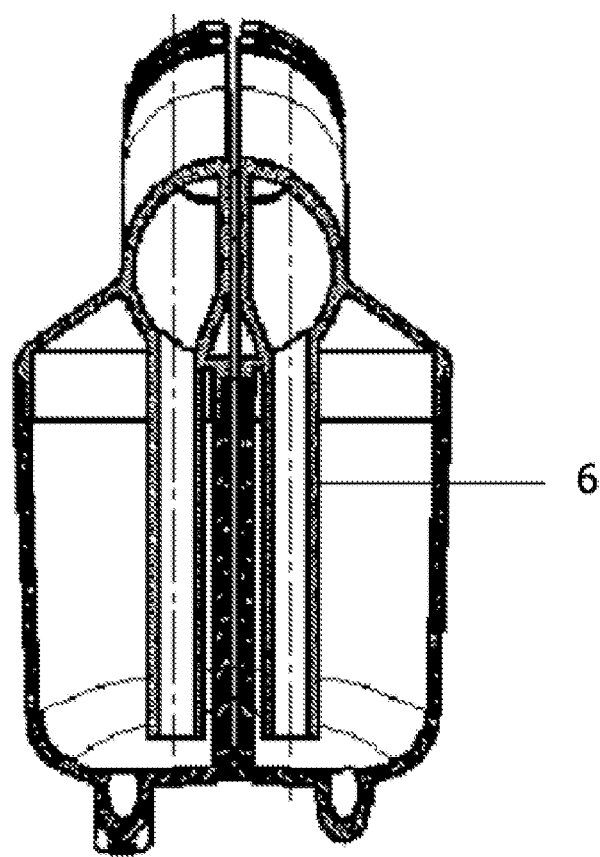
FIG. 7—Is the sectional view of the inner structure of the closed system water trap for a double lumen breathing circuit.
Figure 8:
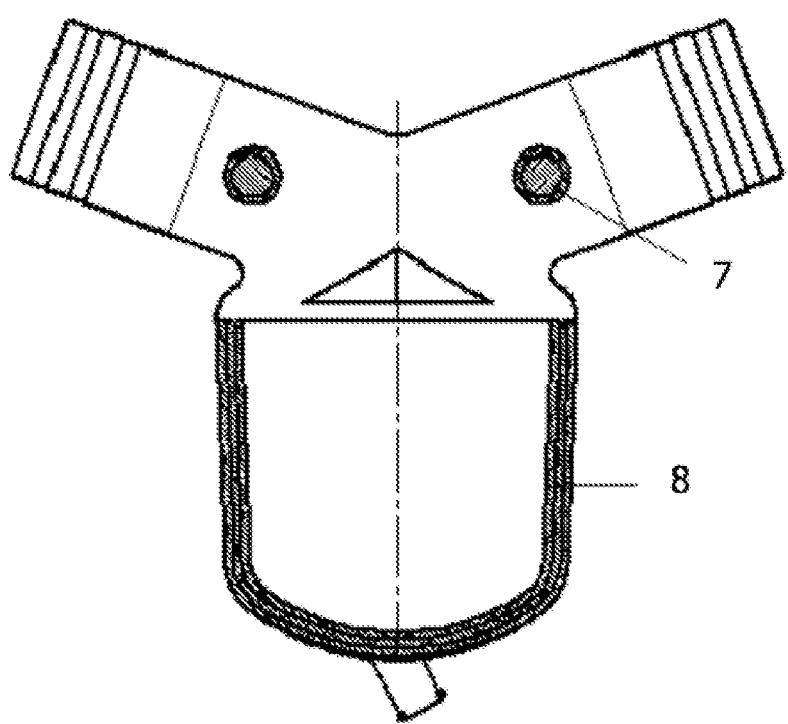
FIG. 8—Is the vertical intermediate sectional view of the closed system water trap for the double lumen breathing circuit.
Figure 9:
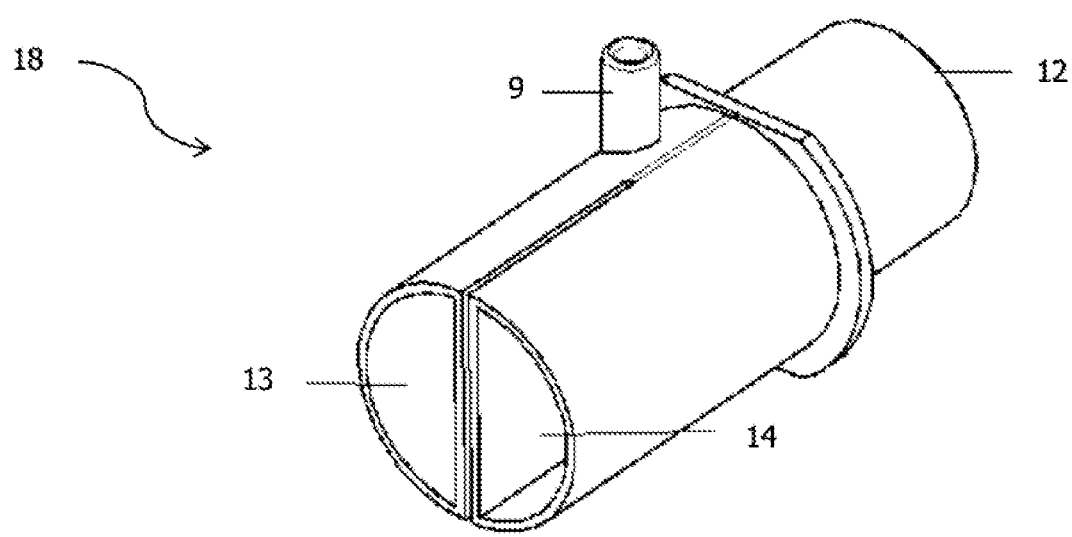
FIG. 9—Is the perspective view of the I connector comprising a lung pressure measurement port for a double lumen breathing circuit.

1. Expiratory line closed system water trap of a coaxial breathing circuit.
2. Closed system water trap for a double lumen breathing circuit.
3. Leg part section
4. Bottle section
5. Needleless grooved luer port
6. Inkwell formation
7. Leg part coupling part 8. Bottle coupling part
9. Lung pressure measurement port
10. Lid
11. Stopper
12. Patient side
13. Tube connection of the expiratory line
14. Tube connection of the inspiratory line
15. Needleless apparatus
16. Inspiratory line closed system water trap of a coaxial breathing circuit.
17. I connector in FIG. 5
18. I connector in FIG. 9

DETAILED DESCRIPTION OF THE INVENTION

The invention subject to the application is related to closed system water trap of double lumen and coaxial breathing circuits (1), (2), and (16), wherein the water accumulated at the bottle section (4) of the coaxial breathing and double lumen circuits having a lung pressure measurement port (4) can be discharged without opening the bottle (4) by means of a drainage needleless grooved luer port (5) and a needleless apparatus (15) attached to the port (5), designed to have an inkwell shape; comprising components such as:

A leg part section enabling connection with the tube of the coaxial breathing circuit, which ensures, the water inside the tube to be directed to the water trap (1), (16), the coupling of the double lumen breathing circuit tube to the fully closed system water trap (2), and the collection of the fluid accumulated in the tubes to pass through inkwell (6) by means of an incline and for said fluid to be collected into the bottle (4), A bottle section (4) which collects the fluid received from the inkwell (6) and the leg part section (3) of the breathing circuit, A needleless grooved luer port (5) which enables the discharging of water collected in the bottle (4) by means of a needleless apparatus (15) and an injector attached thereon, An inkwell (6) which prevents the air flow into the bottle section (4) and which prevents the reflux of the water collected into the bottle (4) back into the breathing circuit until said bottle has been emptied, A leg part section coupling part (7) which enables the fixedly mounting of the symmetrical leg part sections (3) of the double lumen breathing circuit closed system water trap (2), A bottle connection part (8) which enables the fixedly mounting of the symmetrical bottle sections (4) of the double lumen breathing circuit closed system water trap (2), A lung pressure measurement port (9) which can be coupled to the probe that is used to measure the lung pressure of the patient's breath received from the patient in double lumen breathing circuits, A lid (10) which prevents the leakage of the fluid collected inside the bottle section (4) into the tube of the breathing circuit until said fluid has been discharged.

A stopper (11) which prevents the passage of the fluid collected in the bottle (4) from the bottle to the tube before said fluid is discharged and passage of air into the bottle section (4), A patient side (12) which is coupled to the catheter mount or similar apparatus that are directly in contact with the patient, Expiratory line tube connection (13) to which the expiratory line tube is connected, Inspiratory line tube connection (14) to which the inspiratory line tube is connected, A needleless apparatus (15) used to discharge the water collected in the bottle section (4) to be discharged from the grooved luer port (5).

The water traps having conventional structures have been removed and three different, closed system water traps (1), (2), (16) have been re-designed to be suitable with the inspiratory and the expiratory lines of the coaxial breathing circuits and the double lumen breathing circuits, in the double lumen and coaxial breathing circuits having a lung pressure measurement port and closed system water trap that can be discharged with an injector according to the invention. The closed system water trap (1, 2, 16) that is used in breathing circuits is formed of three structures. The leg part section (3) is the structure where the tubes of the breathing circuit are coupled to the water trap, the bottle section is where the water received from the breathing circuits are collected, the inkwell section (6) is the structure which prevents the reflux of the water that has been collected in the bottle section (4) of the water trap.

The leg part section (3) of the coaxial breathing circuit expiratory line closed system water trap (1) has been designed such that the inner tube of the coaxial breathing circuit passes through it, that the water accumulated in the expiratory line is directed towards the water trap, and such that the expiratory air received from patient which passes through the outer tube is not prevented.

The bottle section (4) of the closed system water traps (1, 2, 16), enable the drainage of the accumulated fluid without the necessity to open the bottle (4), by means of a needleless apparatus that has been positioned into the port (5), wherein said drainage needleless grooved luer port (5) is provided at the base of said bottle (4). The inkwell section (6) has an inkwell shape and by this means the water that has accumulated in the bottle (4) has been prevented from leaking back into the tube.

The leg part section (3) of the closed system water trap (16) that is used to couple the inspiratory line tube connections (13) of the coaxial breathing circuits, is positioned between the ventilation/anaesthesia devices and the inspiratory line. A stopper (11) has been placed between the leg part section (3) and the bottle section (4) in order to prevent the reflux of water and a spring has been integrated to the leg part section (3) in order to protect the position of the stopper.

The water that accumulated in the coaxial breathing circuit expiratory line closed system water trap (1), and the double lumen breathing circuit closed system water trap (2) and the coaxial breathing circuit inspiratory line closed system water trap (16), can be discharged without opening the bottle section (4) by means of a drainage needleless grooved luer port (5) located at the bottle section (4), and via a needleless apparatus (15) integrated to this port (5) and via an injector. By this means a fully closed drainage (fluid discharge) is provided and the risk of the nurse or the patient being infected has been overcome. The reflux of the water that has been accumulated in the bottle (4) to the tube before said bottle is discharged and the passage of air to the bottle section (4) is prevented by means of a stopper (11) and an inkwell (6).

The right and left sections of the leg part section (3) and the bottle section (4) are symmetrical with each other in the double lumen breathing circuit closed system water trap (2).

The lung pressure measurement shall be taken by means of the port (5) that has been positioned into the section through which the air received only from the patient passes from the expiratory line tube connection (13) to which the expiratory line tube and the I connector is coupled to, in coaxial breathing circuits and double lumen breathing circuits.

The lung pressure measurement port (9) is located at the line where the breath received from the patient passes through in conventional breathing circuits and it is used to determine if the pressure difference required for the patient to perform respiration is formed or not and to determine if the patient is performing carbon dioxide re-breathing or not.

Figure 1:
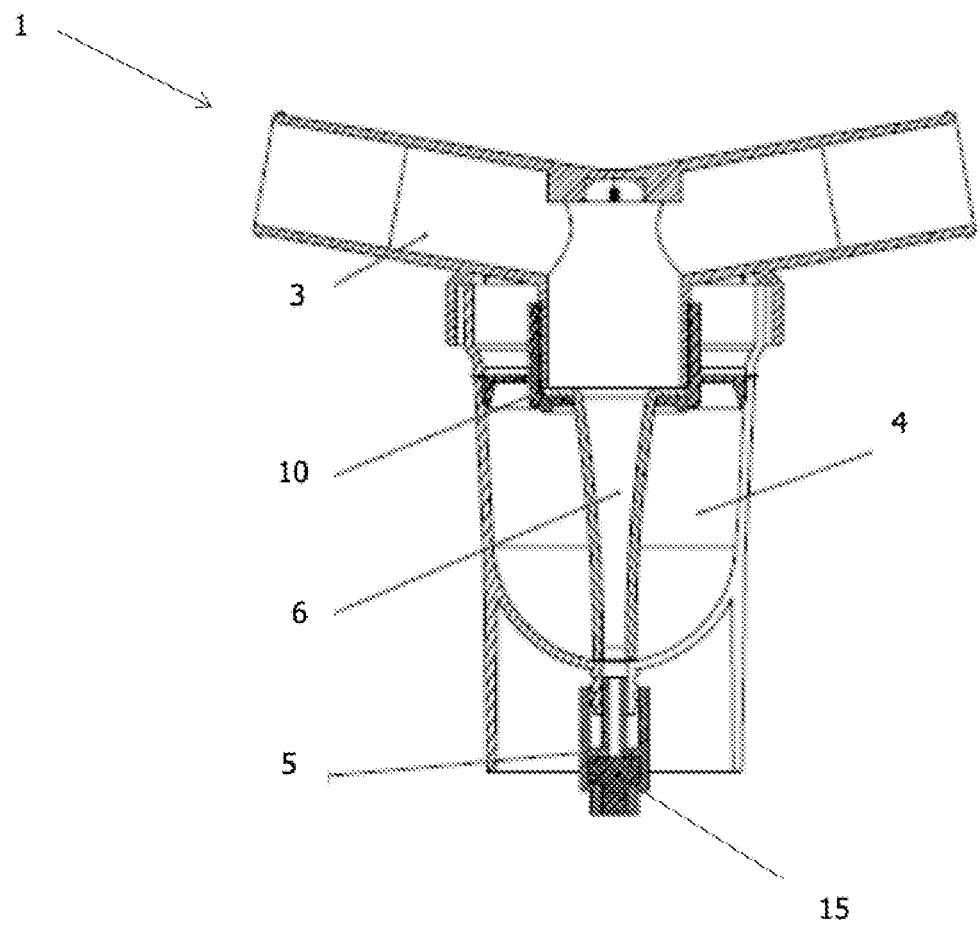
FIG. 1—Is the vertical sectional view of the water trap of the fully closed system expiratory line for a coaxial breathing circuit.
Figure 2:
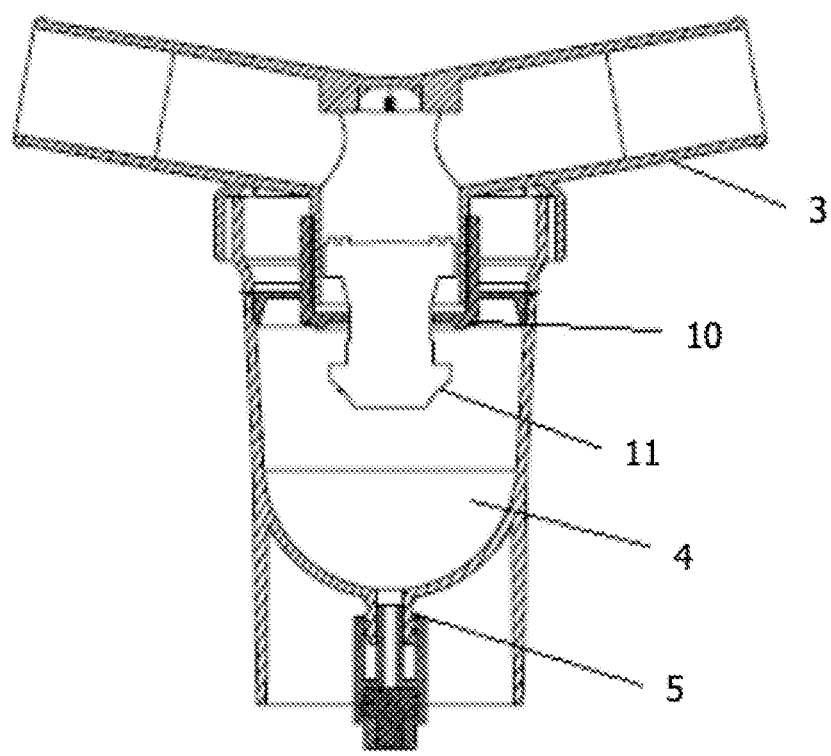
FIG. 2—Is the vertical sectional view of the water trap of the fully closed system expiratory line for a coaxial breathing circuit.
Figure 3:
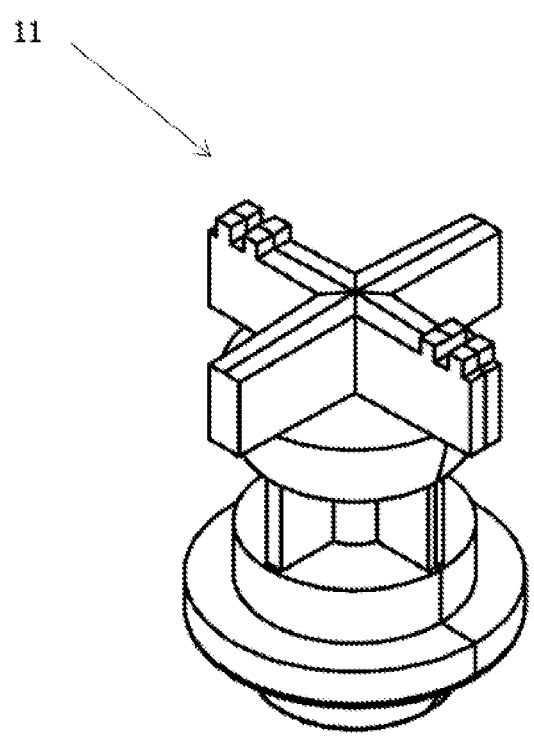
FIG. 3—Is the perspective view of the breathing circuit stopper
Figure 4:
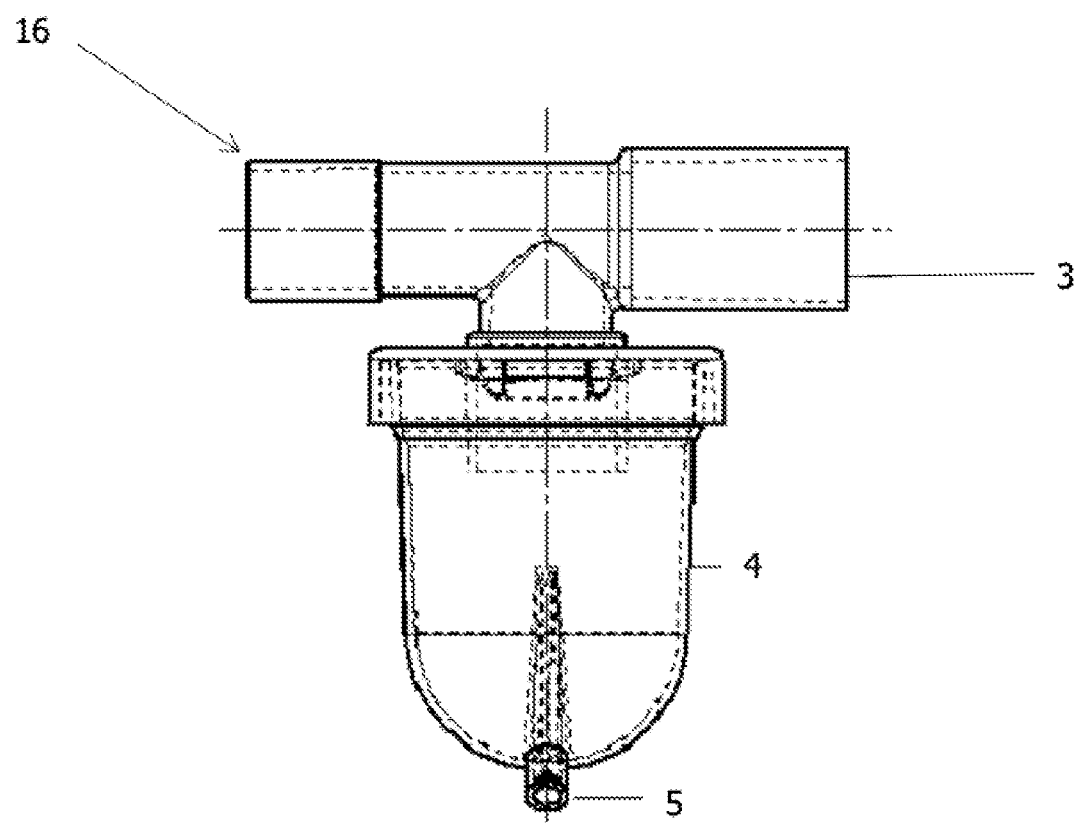
FIG. 4—Is the vertical sectional view of the water trap of the fully closed system inspiratory line for a coaxial breathing circuit.

FIG. 1 is the vertical sectional view of the expiratory line closed system water trap for a coaxial breathing circuit. The leg part section (3) is inserted into the breathing tubes by means of two legs that open into two directions. The water that is accumulated in the expiratory line of the coaxial breathing circuit by means of the angle between the legs (3) is passed through the inkwell (6) section and is collected into the bottle section (4).

By means of the invention the risk of the patients to contract hospital diseases or diseases arising from ventilation is reduced. Also by means of the water traps (1, 2, 16) that are to be used, the air that passes through the breathing circuits will not come across any resistance and the leakage of fluid into both the ventilation and the anaesthesia device is prevented. It has been enabled by means of the closed system water trap (2) that has been developed, for a water trap to be able to be mounted at the middle of the tube which is the section where most of the water accumulated.

As the draining of the fluid accumulated in the closed system water trap (1, 2, 16) are carried out by a closed system drainage needleless grooved luer port (5) it is prevented for the patient or the nurse to be infected.

What is claimed is:

1. A coaxial breathing circuit systems having a lung pressure measurement port and a closed system water trap that can be discharged, comprising:
    a coaxial breathing circuit expiratory line closed system water trap which can be connected to a mid section of an expiratory line of a coaxial breathing circuit and which enables a collection of water accumulated in the expiratory line,
    a first leg part section which provides connection with the coaxial breathing circuit, which directs the water located inside tubes to the coaxial breathing circuit expiratory line closed system water trap,
    a coaxial breathing circuit inspiratory line closed system water trap, which can be connected to a device side end section of an inspiratory line of the coaxial breathing circuit and which enables the collection of the water accumulated in the inspiratory line,
    a second leg part section connects to the coaxial breathing circuit inspiratory line closed system water trap, wherein one side of the second leg part is suitable to be inserted into breathing circuit tubes and another side of the second leg part is suitable to be inserted into an anaesthesia/ventilation device,
    an inkwell, wherein water that is accumulated is passed through by means of an incline to be finally collected in a bottle section, in each of the coaxial breathing circuit expiratory line closed system water trap and the coaxial breathing circuit inspiratory line closed system water trap,
    each bottle section into which water is transferred from each respective inkwell, and each respective first leg part section or second leg part section,
    wherein the coaxial breathing circuit systems further comprise:
    a grooved luer port which enables the discharging of the water collected in the bottle section by means of a needleless apparatus, the grooved luer port has a right angle towards the second leg part section in the coaxial breathing circuit inspiratory line closed system water trap; and which is concealed with a skirt section that extends below the bottle section in the coaxial breathing circuit expiratory line closed system water trap,
    each inkwell which prevents a reflux of the water collected in the bottle section into the breathing circuit tube until said bottle has been drained and which also prevents an air flow into the bottle section,
    the lung pressure measurement port is provided on an I connector in the coaxial breathing circuit,
    a lid which prevents the water that has accumulated in at least one of the bottle sections from entering into an upper section of the coaxial circuit until said accumulated water has been discharged,
    a stopper which prevents the water collected in at least one of the bottle sections from leaking back said water is discharged and which prevents a passage of the air into the bottle section,
    the I connector comprises a patient connection section, the lung pressure measurement port for the coaxial breathing circuit to which a catheter mount can be coupled to,
    an expiratory line tube coupling configured to connect to an expiratory line tube, an inspiratory line tube coupling configured to connect to an inspiratory line tube,
    the coaxial breathing circuit inspiratory line closed system water trap which can be coupled between the coaxial breathing circuit and the anaesthesia/ventilation device and which enables the collection of the water that has accumulated inside the inspiratory line.

2. The breathing circuit systems according to claim 1, wherein the grooved luer port enables discharging of the water that has accumulated in the bottle section of the closed system water traps from the bottle section without opening the bottle.

3. The breathing circuit systems according to claim 1 wherein the water accumulated in the expiratory line of the breathing circuit is passed through the inkwell section by means of an angle between each side of the leg part and then collected into the bottle section.

4. The breathing circuit systems according to claim 1, wherein the systems comprise the lung pressure measurement port which enables to determine if a required pressure difference for the patient to be able to breath is formed or not and if the patient performs carbon dioxide re-breathing or not.

5. The breathing circuit systems according to claim 1, wherein an angle of the leg part section of the coaxial breathing circuit expiratory line closed system water trap enables the passage of the inspiratory tube through it.

6. The breathing circuit systems according to claim 1, wherein the right angle of the needleless apparatus is directed towards the leg part section provided in the coaxial breathing circuit inspiratory line closed system water trap.

7. The breathing circuit systems according to claim 1, wherein the grooved luer port which is concealed with the skirt section extending from below the bottle section is provided in the coaxial breathing circuit expiratory line closed system water trap.

* * * * *

UNITED STATES PATENT AND TRADEMARK OFFICE
CERTIFICATE OF CORRECTION

Page 1 of 1

PATENT NO. : 11,565,070 B2
APPLICATION NO. : 16/802642
DATED : January 31, 2023
INVENTOR(S) : Atilla Sevincli It is certified that error appears in the above-identified patent and that said Letters Patent is hereby corrected as shown below:

On the Title Page

Item (62), Should read:
--The present case is a Divisional of US Patent Application No. 15/745,129 filed 02/27/2020, which is a National Stage Entry of PCT/TR2015/050066 filed on 8-13-2015.--

Signed and Sealed this
Twenty-first Day of November, 2023

Katherine Kelly Vidal
*Director of the United States Patent and Trademark Office*